(12) United States Patent
Freeman et al.

(10) Patent No.: US 6,881,748 B1
(45) Date of Patent: Apr. 19, 2005

(54) DRUG TARGETING

(75) Inventors: Sally Freeman, Cheshire (GB);
Mohammed Jaffor, Manchester (GB);
Ian Stratford, Derbyshire (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/763,236

(22) PCT Filed: Aug. 19, 1999

(86) PCT No.: PCT/GB99/02620

§ 371 (c)(1),
(2), (4) Date: Jun. 11, 2001

(87) PCT Pub. No.: WO00/10611

PCT Pub. Date: Mar. 2, 2000

(30) Foreign Application Priority Data

Aug. 19, 1998 (GB) .............................................. 9818030
Aug. 20, 1998 (GB) .............................................. 9818156

(51) Int. Cl.⁷ ...................... A01N 43/50; A61K 31/415; A61K 31/13
(52) U.S. Cl. ...................... 514/398; 514/396; 514/385; 514/398; 514/655; 514/650; 514/654; 514/659
(58) Field of Search ................................ 514/385, 396, 514/398, 655, 650, 654, 659

(56) References Cited

U.S. PATENT DOCUMENTS 4,261,883 A * 4/1981 Smolarsky ................... 530/302
5,652,255 A    7/1997 Adams et al.

OTHER PUBLICATIONS

Lipman, Curr Rheumatol Rep, Dec. 2001:3(6) 513–9.*

Hay et al, "Nitroimidazole–based 'extruded mustards' designed as reductively activated hypoxia–selective cytotoxins", Chemical Abstracts 125:211954.

Palmer et al, "Reductive Chemistry of the Novel Hypoxia–Selective Cytotoxin 5–[N,N–Bis(2–chloroethyl)amino]–2, 4–dinitrobenzamide", Chemical Abstracts 122:230131 (1995).

Atwell et al, "Relationship between structure and kinetics of cyclization of 2–aminoaryl amides: potential prodrugs of cyclization–activated aromatic mustards", Chemical Abstracts 120:216381.

Jenkins et al, "Synthesis and evaluation of α–[(2–haloethyl)=amino)methyl]–2–nitro–1H–imidazole–1–ethanols as prodrugs of α–[(1–aziridinyl)methyl]–2–nitro–1H–imidazole–1–ethanol (ESU–1069) and its analogs which are radiosensitizers and bioreductively activated cytoxins", Chemical Abstracts 113:171945 (1990).

Siim et al "Nitro reduction as an electronic switch for bioreductive drug activation", Chemical Abstracts 128:238843 (1998).

Hay et al, "Nitroimidazole–based "extruded mustards" designed as reductively activated hypoxia–selective cytotoxins", Anti–Cancer Drug Design 11(5):383–402 (1996).

Rauth et al, "Bioreductive therapies: An overview of drugs and their mechanisms of action", International Journal of Radiation 42(4):755–762 (1998).

Nudelman et al "Hypoxic radiosensitizers: substituted styryl derivatives", Arch. Pharm. 327(10):619–625 (1994).

Jaffar et al, "Bioreductive drugs: Selectivity towards hypoxic tissue", Expert Opinion on Therapeutic Patents 9(10):137 1380 (1999).

* cited by examiner

*Primary Examiner*—Russell Travers
*Assistant Examiner*—Shahnam Sharareh
(74) *Attorney, Agent, or Firm*—Nixon & Vanderhye P.C.

(57) ABSTRACT

A bioreductive conjugate comprises a bioreductive moiety with at least one therapeutic agent linked thereto and physiologically acceptable derivatives thereof. The bioreductive moiety incorporates an aromatic ring substituted with a nitro group and the conjugate is such that bioreduction of the nitro group causes release of the therapeutic agent by a through bond elimination and the residue of the bioreductive moiety to undergo an intramolecular cyclization reaction in which the nitrogen of the original nitro group provides an atom of the thus formed ring.

9 Claims, No Drawings

DRUG TARGETING

This application is the U.S. national phase of international application PCT/GB99/02620 filed Aug. 19, 1999, which designated the US. PCT/GB99/02620 claims priority to GB Application No. 9818030.0 filed Aug. 19, 1998 and GB Application No. 9818156.3 filed Aug. 20, 1998.

The present invention relates to bioreductuve drug conjugates for use in targeting of therapeutic agents to localised regions of hypoxic and/or ischemic tissue within the body.

Reduced oxygen tension (hypoxia) has been demonstrated in a variety of medical conditions. Thus for example, it has been demonstrated to be present in tumours and in fact it has long been suspected that oxygen deficiency in tumours may be a limiting factor in the control of tumours by radiotherapy. Furthermore, it is disclosed in copending U.K. Patent Application No. 9719059.9 that in patients suffering from rheumatoid arthritis (a common systemic inflammatory disease which predominantly affects the synovial joints) the synovial tissues are profoundly hypoxia and contain high levels of reductases. Hypoxic tissue is also a feature of various fibrotic disorders and psoriasis.

Relatively recently, the presence of hypoxia in tumours has been exploited in their treatment by the use of bioreductive drugs, i.e. drugs which require metabolic reduction to generate cytotoxic metabolites. This process is facilitated by the presence of appropriate reductases and the lower oxygen conditions present in some cancerous (hypoxic) as compared to normal (normoxic) tissue. As a result, a number of bioreductive drugs capable of producing cytotoxic metabolites under hypoxic conditions have been proposed for use in combination with radiotherapy treatment of tumors.

A number of bioreductive compounds are known to act as potent alkylating agents after undergoing reduction in vivo. Examples of known bioreductive alkylating agents include compounds such as activated enamines, vinylogous quinone methides, simple quinone methides and α-methylene lactones or lactams. Bioactivation of such compounds produces species which are electron deficient and which are capable of covalent binding to a nucleophilic centre on a biomolecule, such as DNA.

Most bioreductive drugs that have been developed for use in the treatment of tumors exhibit an optimum "trapping" potential when hypoxia is profound ($pO_2$<12 mm Hg) and this is believed to form the basis for their selectivity for cancerous as opposed to normal tissues.

Bioreductive drugs have also been proposed for use in several methods for the detection of hypoxic cells in tumors. In this way, radiotherapy treatment may be optimised for individual patients on the basis of the oxygen status of their tumors. Thus, for example, U.S. Pat. No. 5,086,068 describes the use of nitroaromatic compounds in the detection of hypoxic cells in normal and tumor tissue. An immunogenic conjugate comprising a nitroaromatic compound and an immune response inducing carrier is used in vitro to raise antibodies specific to the nitroaromatic compound. These antibodies are in turn used to detect the presence of hypoxic tissue following in vivo administration of the nitroaromatic compound.

A number of methods have also been described for detecting the presence of hypoxic cells in tumors using labelled 2-nitroimidazole in which labelled fragments of the nitroimidazole compound bind to cellular macromolecules. More recently, the use of an immunologically detectable hapten such as theophylline covalently bound to a 2-nitroimidazole has been suggested as a method of identifying hypoxic cells (see Brit. J. Cancer 63: 119–125, 1991 & 72: 1462–1468, 1995, and Anti-Cancer Drug Design 10: 227–241, 1995). Bioreduction of the nitroamidazole leads to binding of bioreductuve metabolites, and hence the theophylline side-chain, to intracellular molecules. Immunochemical techniques are then used to stain and thus locate those cells containing the bound theophylline.

Other agents comprising a bioreductuve moiety, e.g. 2-nitroimidazole, for the diagnosis or treatment of hypoxic cells are described in U.S. Pat. No. 5,387,692.

A number of bioreductive agents have been described for use in the delivery of cytotoxic drugs to hypoxic tumor tissue in which bioreductive activation at the tumor site results in selective delivery of the drug. However, following drug delivery the bioreductive compound remaining in the tissues is itself a potential alkylating agent and thus cytotoxic, thereby rendering such a system entirely unsuitable for use as a non-cytotoxic drug delivery vehicle in diseases other than cancer. Hypoxia-selective bioreductive drug delivery agents proposed for use in anti-tumor therapy are described, for example, in Dissabs 87:31004, 1987 and in J Med. Chem. 34: 2933–2935, 1991.

Delivery systems which utilise bioreduction to deliver a non-cytotoxic drug species have also been proposed. For example, a delivery system based on quinone propionic acid has been described (see Pharmaceutical Research 8(3): 323–330, 1991) in which the benzoquinone acts as the trigger and the propionic acid moiety allows for linkage either to an amine moiety (e.g. an enzyme inhibitor) or to an alcohol (e.g. a steroid). Two electron activation of the benzoquinine trigger facilitates intramolecular cyclization generating a stable lactone, a process which results in elimination of the drug species. However, the lactone produced is itself a potential alkylating agent. This system is thus unsuitable for use as a non-cytotoxic drug delivery system. Furthermore, in aqueous solution in the absence of a reducing agent the lactone produced following drug delivery is very unstable and undergoes degradation. The instability of this prodrug system in aqueous solution thus precludes its use for drug delivery in vivo.

WO-A-98/35701 (PCT/GB98/00461—Theramark Ltd.) discloses bioreductive conjugates comprising a non-cytotoxic bioreductive moiety with at least one therapeutic agent linked thereto which is intended to be released at a hypoxic site. The conjugate is such that after release of the therapeutic agent the bioreductive moiety is itself a stable non-cytotoxic species or reacts with itself to form a stable, non-cytotoxic species. This minimises direct interaction of the carrier with DNA or other biomolecules thus avoiding potential mutagenic side effects. Thus, for example, in preferred conjugates as disclosed in the PCT application the bioreductive moiety is a benzoquinone nucleus. On reduction of the benzoquinone nucleus at the hypoxic site, the therapeutic agent is released and the residue of the bioreductive moiety participates in an intramolecular rearrangement and/or cyclisation reaction to generate a non-cytotoxic species.

According to a first aspect of the present invention there is provided a bioreductive conjugate comprising a bioreductive moiety with at least one therapeutic agent linked thereto and physiologically acceptable derivatives thereof wherein the bioreductive moiety incorporates an aroipatic ring substituted with a nitro group and the conjugate is such that bioreduction of the nitro group causes release of the therapeutic agent by a through bond elimination and the residue of the bioreductive moiety to undergo an intramolecular cyclisation reaction in which the nitrogen of the original nitro group provides an atom of the thus formed ring.

According to a second aspect of the present invention there is provided a therapeutic composition comprising a bioreductive conjugate as defined in the previous paragraph in conjunction with a therapeutically acceptable carrier.

According to a third aspect of the present invention there is provided the bioreductive conjugate for use in a therapeutic method.

According to a fourth aspect of the present invention there is provided the use of the bioreductive conjugate for the manufacture of a medicament for therapeutic treatment.

According to a sixth aspect of the present invention there is provided a method of therapeutic treatment comprising administering to a subject in need of such treatment a therapeutically effective amount of the bioreductive conjugate.

Preferably the bioreductive moiety is non-cytotoxic.

As used herein, "non-cytotoxic bioreductive moiety" means that the bioreductive moiety has substantially no cytotoxic activity in vivo. Thus it is intended that the preferred bioreductive moiety for use in accordance with the invention is not only in itself non-cytotoxic, but that this produces substantially no cytotoxic species following bioreductive activation. By "non-cytotoxic" it is meant that the bioreductive moiety does not interact directly with DNA. Preferably, the bioreductive moiety is substantially non-mutagenic. Thus, the preferred bioreductive moiety is intended to function merely as a non-cytotoxic carrier or targeting agent for the drug species which, following delivery of the drug at the target site, is eliminated from the body in the absence of any undesirable side-effects.

In accordance with the invention the bioreductive moiety incorporates an aromatic ring substituted with a nitro group which is capable of being reduced (e.g. to an amino or hydroxylamino group) in a hypoxic environment by reducing enzymes or reductases (e.g. P450 reductase). It is this reduction which provides for release of the therapeutic agent (by through bond elimination) and formation (by an intramolecular cyclisation reaction) of a ring system which will generally fused with the aromatic ring and which incorporates, as a ring atom, the nitrogen atom of the nitro group.

It is preferred that formation of the ring occurs as a result of a self-alkylation reaction, particularly by interaction of the reduced from of the nitro group with an olefinic double bond. The formation of this ring (i.e. that containing the nitrogen atom of the nitro group) ensures that the residue of the bioreductive moiety provides a stable species without a reactive alkylating centre and can therefore be non-cytotoxic. The ring system will for preference have 5 to 7 ring atoms (as this will favour the cyclisation).

The following reaction Schemes 1 and 2 illustrate for examples of compounds in accordance with the invention, the manner in which drug release and intramolecular cyclisation may occur.

Scheme 1

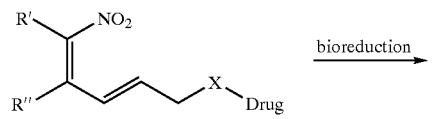

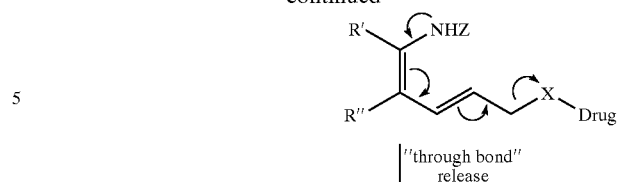

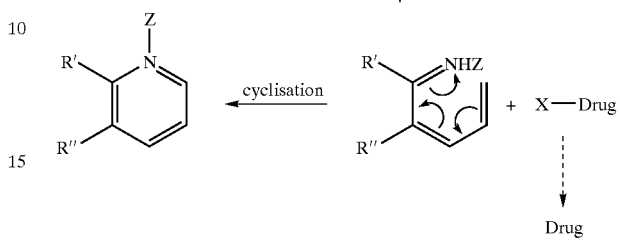

Scheme 2

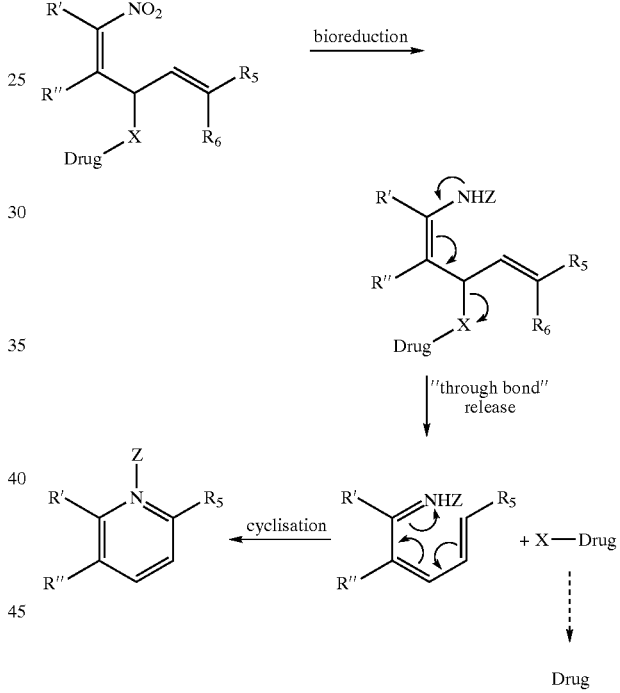

In the above schemes, R' and R" (together with the bonds by which they are connected) form an aromatic ring, Z is H or OH, and X is a linker group (which may be part of the drug) by means of which the drug residue is bonded to the aromatic ring. Reduction of the nitro group will initially yield the hydroxylamine compound (Z=OH) and subsequently the amine (Z=H), the former being, about 100-fold more reactive than the latter.

Although the conjugate is capable of undergoing bioreduction, it should be substantially stable in a non-oxygenated environment.

The bioreduction of a nitro group (bonded to an aromatic ring) to initiate release of the therapeutic agent is convenient since the reduction potential of the nitro group may be made commensurate with the oxygen potential found in hypoxic tissue and nitro-substituted aromatic ring systems are readily synthesised. For preference the one electron reduction potential in water at pH 7 versus the normal hydrogen electrode of the nitro group in the conjugates of the invention is −250 to −450 mV. Furthermore, by the use of appropriate additional substituents bonded to the aromatic ring it is possible to "tune" the reduction potential of the nitro group to the oxygen potential of a particular hypoxic tissue to be targeted thus making the conjugate highly selective. The choice of substituent(s) will also govern the ability of the conjugate penetrated tissues so it is possible to design conjugates which have the ability to poorly penetrate perfused tissues and only release the drug in a hypoxic and/or ischemic environment.

The "aromatic ring" to which the nitro group is bonded is a ring system incorporating an aromatic sextet of electrons and covers such rings which are comprised wholly of carbon atoms or which include at least one heteroatom. If more than heteroatom is present then the heteroatoms of the ring may be the same or different. The aromatic ring may have 5 to 12, preferably 5 or 6 carbon atoms. Examples of aromatic rings which may be employed for the conjugate include those derived from benzene, pyrrole, imidazole, thiophene, furan, oxazole, thiazole, triazole, and tetrazole. The aromatic ring may be part of a fused ring system in which the other ring or rings may be carbocyclic or heterocyclic and aromatic or non-aromatic.

In conjugates in accordance with the invention, the aromatic ring will generally be substituted with a single nitro group capable of effecting, on reduction thereof, release of one molecule of therapeutic agent (with associated intramolecular cyclisation reaction). However we do not preclude the possibility of a single nitro group on the ring providing (on reduction) for release of two or more molecules of therapeutic agent or the possibility that the ring includes two or more nitro groups each capable (on reduction) of effecting release of separate molecules of therapeutic agent. Furthermore, the conjugate may have two or more aromatic rings substituted with nitro groups which effect release of respective molecules of therapeutic agents in the manner described above.

In preferred conjugates of the invention, the residue of the drug to be released on bioreduction is bonded to the aromatic ring via a side chain attached to an atom of the aromatic ring adjacent to that to which the nitro group is bonded.

In the following description, the term "drug moiety to be released" is intended to cover the possibilities of the release of a residue of the drug per se (i.e. where X above is part of the dug) or release of the combination of the drug residue and the linker (where the drug is bonded to the bioreductive moiety via a linker).

In a preferred conjugate of the invention, the drug moiety to be released on bioreduction is bonded to the aromatic via a side chain incorporating one or more double bonds which are located in the side chain between said moiety and the aromatic ring, which is/are conjugated to the aromatic ring, and which is/are displaceable to provide for elimination of moiety and formation of an arrangement of double bonds such that the residue of the bioreductive moiety is capable of undergoing the intramolecular cyclisation reaction. On bioreduction, there is an electron shift from the nitrogen atom of the reduced form of the nitro group towards and around the aromatic ring and into the linker group to result in displacement of the therapeutic agent. As a result, there is formed a residue of the bioreductive moiety from which the aromaticity has been lost and which has adjacent exocyclic amino and diene groups together capable of forming a six membered ring with regeneration of aromaticity. (See scheme 1 above illustrating the mechanism of release to a specific compound in accordance with the embodiment of the invention). This will generally imply that the drug moiety to be released will be bonded to a carbon atom of the side chain which is adjacent to a (conjugated) double bond in the side chain.

Examples of compounds in accordance with this embodiment of the invention are of the general formula (I)

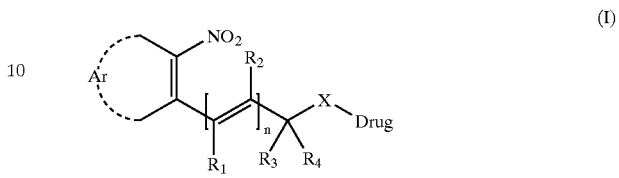

in which
the dashed lines represent completion of a substituted or unsubstituted aromatic ring system;
Drug is a therapeutic agent;
X is a linker (which may be part of the drug) and may for example be O, —NH, S, an amide, alcohol, phenol, carboxylic acid (carboxylate), carbonate, phosphate, sulphate or sulphonate:
$R_1$, $R_2$, $R_3$ and $R_4$ are independently hydrogen, substituted or unsubstituted alkyl (e.g. $C_{1-4}$), aryl, halide, amine, alkoxy, ether, ester, alcohol, phenol, nitro, amide, thiol, sulphate, phosphate, phosphonate; and
n is 1 to 3.
Preferably n=1 whereby the drug moiety to be released is bonded to the aromatic ring via a propenyl side chain.

If the aromatic ring system is substituted then the substituents may be selected from the same as those for $R_{1-4}$.

More specific examples of compounds in accordance with this embodiment of the invention are of the formulae (II)–(III).

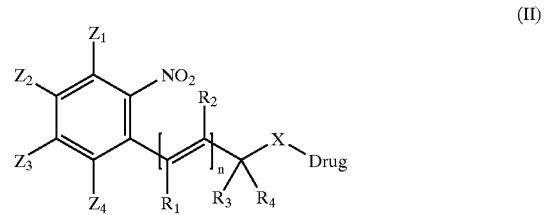

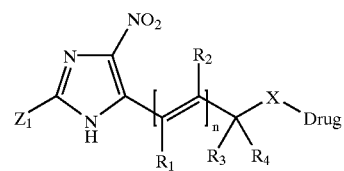

in which $Z_1$, $Z_2$, $Z_3$ and $Z_4$ are the same or different and are selected from the same groups as defined above for $R_1$–$R_4$.

Examples of the substituents for $Z_1$, $Z_2$, $Z_3$ and $Z_4$ include, but are not limited to substituted or unsubstituted alkyl, aryl, amino, ether, ester, alkoxy or sulphonamide groups. Alternatively two (preferably adjacent) Z substituent groups of the aromatic ring may, together with the ring atoms to which they are attached, form a carbocyclic or heterocyclic aromatic or non aromatic ring.

Although preferred compounds in accordance with the first embodiment of the invention have been illustrated for the case in which the aromatic ring is a benzene or imidazole nucleus it will be appreciated that corresponding conjugate may be produced with other aromatic ring systems, e.g.

unsubstituted or substituted ($Z_{1-4}$) pyrrole, thiphene, furan oxazole, thiazole, triazole and tetrazole rings.

In further preferred conjugates in accordance with the invention, the drug moiety to be released on bioreduction is bonded to the carbon atom adjacent to the aromatic ring of a side chain bonded to that ring (i.e. the benzylic position in the case where the aromatic ring includes a benzene ring) and that carbon atom is bonded to an olefinic double bond of the side chain. (See Scheme 2 above illustrating the mechanism of release for a specific compound in accordance with this embodiment of the invention).

Examples of compounds in accordance with this embodiment of the invention are of the formula (IV).

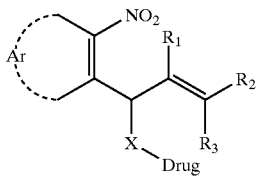

(IV)

in which

Drug and X are as defined above;

the dashed lines represent completion of a substituted or unsubstituted aromatic ring; and $R_{1-3}$ are the same or different and are as defined above.

Examples of compounds in accordance with this embodiment of the invention are of the formula (V)–(VI).

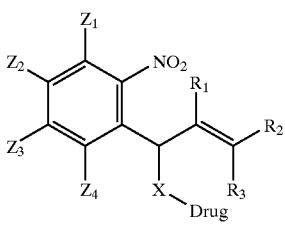

(V)

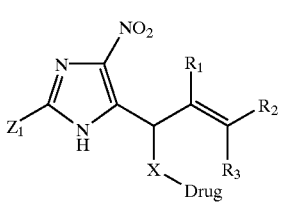

(VI)

Although preferred compounds in accordance with the second embodiment of the invention have been illustrated for the case in which the aromatic ring is a benzene or imidazole nucleus it will be appreciated that corresponding conjugate may be produced with other aromatic ring systems, e.g. unsubstituted or substituted ($Z_{1-4}$) pyrrole, thiophene, furan, oxazole, thiazole, triazole and tetrazole rings.

As described above, compounds in accordance with the first and second embodiments of the invention may include various substituents ($Z_{1-4}$) for the aromatic ring. These substituents may be chosen having regard to a number of factors. Thus for example the substituent(s) may be chosen to provide a reduction potential for the nitro group within a particular range. Thus, in the case of conjugates in which the nitro group is bonded to a benzene ring, it may be necessary to have a further ortho-, meta- or para- nitro group bonded to the ring so that the former nitro-group has a one electron reduction potential in water at pH 7 versus the normal hydrogen electrode in the range −250 mV to −450 mV. Nitroimidazoles will generally have a reduction potential within the required range without substitution by a further nitro group. Alternatively or additionally the aromatic ring may have a substituent such as to give a particular reduction potential to make the conjugate selective for a particular hypoxic site being targeted. Alternatively or additionally, the substituent(s) may be chosen to provide the required characteristics for the conjugate (e.g. solubility) to ensure that it is able to reach the targeted site.

Reductases known to be involved in activation of bioreductive compounds include DT diaphorase, cytochrome P450, NADPH-dependent cytochrome P450 reductase and xanthine oxidase. The ease of reduction of any given bioreductive agent will depend upon its ability to act as a substrate for the intracellular reductases and the expression levels of such enzymes within the particular cell type. The choice of bioreductive compound for use in the invention will thus depend upon the type of enzymes present at the target site. Indeed, it may be useful to determine the relative enzyme activities in the target tissues of individual patients before starting treatment.

It is clearly desirable that the bioreductive conjugate should reach the target site intact. Since bioreduction of the conjugate is dependent upon the redox potential of the bioreductive moiety present, this may be selected such that this is less susceptible to reduction by ubiquitous systems such as NADH or NADPH, thereby increasing the chances that the conjugate will reach the target site still intact. In general, those bioreductive compounds having an optimal redox potential will be more selective in targeting of hypoxic cells and are thus preferred for use in the invention.

The invention is considered to have utility in connection with the delivery of a wide range of therapeutic agents. The expressions "therapeutic agent" and "drug" are used interchangeably herein and are intended to define any atom, ion or molecule which in vivo is capable of producing an effect detectable by any chemical., physical or biological examination. A therapeutic agent will in general by any substance which may be administered to a human or non-human animal body to produce a desired, usually beneficial, effect and may be an agent having either a therapeutic or a prophylactic effect.

Examples of therapeutic agents suitable for use in accordance with the invention include agents in all of the major therapeutic areas including anti-infectives such as antibiotics and antiviral agents, analgesics, anaesthetics and anti-inflammatory agents. Anti-neoplastics, including known cytotoxic agents may also be used. The exact choice of therapeutic agent will naturally depend upon the desired therapeutic application.

Whilst it is envisaged that in general the therapeutic agent will itself be non-cytotoxic, the bioreductive carrier may be used to deliver cytotoxic agents, e.g. in anti-tumor treatment.

Examples of other therapeutic agents for use in accordance with the invention include agents administered to the human or animal body for diagnostic purposes, e.g. for use in radioimaging techniques. In this regard, a radiolabelled steroid may be linked to a non-cytotoxic bioreductive compound for use in the detection of hypoxic cells in tumor tissues.

Methods for attaching bioreductive compounds to a therapeutic agent are within the level of skill in the art. In general, the conjugates in accordance with the invention can be prepared by linkage of a non-cytotoxic bioreductive moiety to at least one therapeutic agent. Linkage of the therapeutic agent to the bioreductive moiety may be effected through any reactive group and standard coupling techniques are known in the art.

Compounds of formula (II) in which $Z_{1-4}$ and $R_{1-4}$ are hydrogen and n=1 may be produced in accordance with the following reaction scheme.

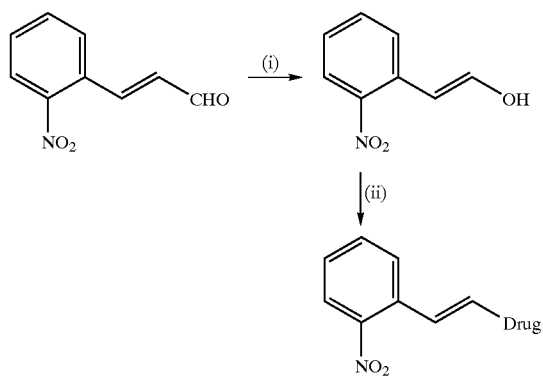

Reagents and conditions: (i) $NaBH_4$, MeOH; (ii) drug—$CO_2H$ or $SOCl_2$/THF then drug—NH.

The substituted derivatives may be produced in analogous manner.

Preferred reaction conditions, e.g. temperature, solvents, etc. depend primarily on the particular reactants and can readily be determined by those skilled in the art. In general, any reactive groups present, e.g. amino, carboxyl etc. will be protected during coupling of the bioreductive with the therapeutic agent, although it is possible to leave some groups unprotected. After coupling, the resulting compound may be purified, e.g. by chromatography.

The bioreductive moiety may be bonded directly to the therapeutic agent or may be bonded to a linker group, X. Linkage between the bioreductive and the therapeutic agent may be effected via any reactive group present in the bioreductive moiety, e.g. a primary amine, carboxylate, alcohol, thiolate, etc. Preferably the bioreductive moiety is linked to the therapeutic agent via an ester, phosphate ester, ether, amine, thiol or thiol ester bond or any combination thereof.

The linker group serves to link the bioreductive moiety to at least one therapeutic agent. Besides filling this role as a linker, the linker group may be selected to yield a bioreductive conjugate having desired characteristics. For example, appropriate choice of a linker group may serve to enhance the resistance of the conjugate to non-bioreductive metabolism and/or enhance delivery of the drug molecule at the target site. It may also be possible to optimise the redox potential, enzyme or tissue specificity, or the solubility of the conjugate by attaching or to incorporating within the linker group appropriately selected moieties, e.g. groups which are tissue targeting. Thus, the ability to alter the nature of the linker group provides for the possibility of altering the physiochemical properties, e.g. solubility, and biological properties, e.g. biodistribution, of the bioreductive conjugate. The primary function of the linker is however to link together the bioreductive compound and the drug.

Linker groups X particularly suitable for use in the invention for those drugs having a free —OH or —SH group include the following in which E represents the residue of a drug species:

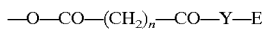

and

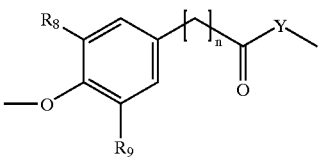

(wherein n is an integer from 1 to 3);

Y represents a sulphur or oxygen atom which may form part of the drug molecule E;

and $R^8$ and $R^9$ each independently represent F or Cl).

There are believed to be many conditions which may benefit from the drug delivery system of the invention. These are primarily conditions associated with hypoxia and/or ischemia. Hypoxia is any state in which a physiologically inadequate amount of oxygen is available to, or utilised by, any given tissue or group of tissues within the body. Ischemia is any local diminution in the blood supply to any tissue in the body and may arise as a result of obstruction in the flow of arterial blood or vasoconstriction. In general, ischemia will ultimately lead to hypoxia.

In a clinical setting, tissues may become hypoxic and/or ischemic as a result of a number of different conditions in the body. Reduction of the blood supply to body tissue has the effect of inducing ischemia, for example in atherosclerosis, diabetes or following tissue or organ transplantation. Inflammatory or cancerous response may also lead to the tissue either physically or metabolically outgrowing its vascular supply, again leading to ischemia and/or hypoxia.

Non-limiting examples of conditions which may be treated using the bioreductive conjugates of the invention include inflammatory conditions. e.g. rheumatoid arthritis, other arthritic conditions such as osteoarthritis, diabetes, atherosclerosis, stroke, sepsis, Alzheimer's disease and other neurological diseases, cancer, kidney disease, digestive diseases and liver disease. Other conditions of interest include chronic periodontitis and ischemia following tissue transplantation.

The bioreductive conjugates of the invention may also find use in the treatment of a wide range of inflammatory conditions in which hypoxia and/or ischemia may be implicated, in particular in treating inflammatory conditions of the soft tissues. In the case of certain inflammatory conditions of the gastrointestinal tract, sections of the tract become hypoxic. Other inflammatory conditions which may be treated in accordance with the invention thus include gastrointestinal disorders such as Crohn's disease.

The compounds of the invention may also be used in the treatment of muscular disorders associated with hypoxia and/or ischemia.

Further conditions include the healing of wounds (acute and chronic), and the treatment of fibrotic disorders, ulcer-active colitis, inflammatory bowel disease, epilepsy, cardiovascular reperfusion injury, cerebral reperfusion injury, hypertensions, cystic fibrosis, psoriasis, para-psoriasis, peptic ulcers, gastric ulcers, duodenal ulcers, diabetic ulcers, dementia oncology and AIDS.

It is believed that many known drugs could have enhanced therapeutic effects if selectively delivered to ischemic/hypoxic tissue. For example, following cerebral attack, cerebral perfusion is reduced and the brain suffers an inflammatory response. The linkage of a vasodilator, such as a nitric oxide generator, or an anti-inflammatory agent, such as a steroid, to a bioreductive agent would thus serve to enhance the therapeutic index of the drug.

Rheumatoid arthritis is known to be associated with chronic synovial inflammation and poor perfusion of the synovial tissues. However, we have now discovered that in patients suffering from rheumatoid arthritis the synovial tissues are in many cases profoundly hypoxic ($pO_2$<12 mm Hg). We have also found that such tissues contain high levels of reductases. Whilst not wishing to be bound by theoretical considerations, it is believed that there are pockets in the synovium which are hypoxic and that is the hypoxic cells in the synovium which are primarily responsible for the inflammation associated with rheumatoid arthritis. Linkage of an anti-inflammatory agent, such as a non-steroidal anti-inflammatory agent, e.g. dexamethasone, a steroid or a nitric oxide inhibitor would thus serve to greatly increase the therapeutic index of the active agent in the treatment of rheumatoid arthritis, whilst at the same time reducing the risk of systemic side effects. The weak acidic based NSAIDs which undergo ion-trapping in acidotic tissue are considered particularly suitable.

Following transplantation and tissue rejection, both ischemia and an immunological-inflammatory response may contribute to tissue hypoxia. Again, such conditions may thus be treated using a conjugate of the invention in which a bioreductive moiety is linked to a vasodilator or to an anti-inflammatory compound or immunological suppressant.

Many of the basic complications of diabetes are believed to owe their basic pathology to hypoxia. Indeed, in many cases diabetics show accelerated atherosclerosis. The present invention may thus be used in the treatment of diabetes by linking a drug, such as a phosphodiesterase inhibitor, to a non-cytotoxic bioreductive moiety.

Hypoxic tissues are also believed to be present in chronic periodontitis, a condition associated with server inflammation of the periodontium. Linkage of an antibiotic or other drug known for treating periodontitis, e.g. a metalloproteinase inhibitor, to a bioreductive may thus be beneficial in treating this condition.

An example of an agent which may be linked to a non-cytotoxic bioreductive compound for use in treating diabetes is dipyridamole.

Viewed from a yet further aspect, the invention provides the bioreductive conjugate of the first aspect of the invention for use in a method of targeting a therapeutic agent to a specific tissue site within the body, in particular to a site of hypoxia and/or ischemia, e.g. in the treatment of rheumatoid arthritis or other arthritic conditions, diabetes, atherosclerosis, stroke, sepsis, Alzheimer's disease and other neurological disorders, cancer, kidney disease, digestive diseases, liver disease, wounds, fibrotic disorders, chronic peridontitis or ischemia following tissue transplantation.

In a preferred embodiment of this further aspect the invention provides that the bioreductive conjugate comprises bioreductive moiety linked to an anti-inflammatory agent for use in the treatment of rheumatoid arthritis.

Viewed from a yet further aspect the invention provides the use of the bioreductive conjugate according to the first aspect of the invention as hereinbefore defined in the manufacture of a medicament for use as a targeting agent, in particular as an agent capable of targeting a site of hypoxia and/or ischemia within the body, e.g. in the treatment of rheumatoid arthritis and other arthritic conditions, diabetes, atherosclerosis, stroke, sepsis. Alzheimer's disease and other neurological disorders, cancer, kidney disease, digestive diseases, liver disease, wounds, fibrotic disorders, chronic periodontitis or ischemia following tissue transplantation.

In another aspect of the invention provides a method of targeting hypoxic and/or ischemic tissues in the human or non-human, preferably mammalian, body comprising administering to said body a bioreductive conjugate in accordance with the first aspect of the invention. In particular, the invention provides a method of treating or preventing rheumatoid arthritis and other arthritic conditions, diabetes, atheroscolerosis, stroke sepsis, Alzherimer's disease and other neurological disorders, cancer, kidney disease, digestive diseases, liver disease, wounds, fibrotic disorders, chronic peridontitis or ischemia following tissue transplantation, said method comprising administering to a human or non-human animal body in need thereof an effective amount of bioreductive conjugate as hereinbefore defined.

Viewed from a yet further aspect the invention provides a pharmaceutical composition comprising a bioreductive conjugate in accordance with the first aspect of the invention or a pharmaceutically acceptable derivative thereof together with at least one pharmaceutical carrier excipient.

The active ingredient in such compositions may comprise from about 0.1% to about 99% buy weight of the formulation. By "pharmaceutically acceptable" is meant that the ingredient must be compatible with other ingredients of the compositions as well as physiologically acceptable to the patient.

Pharmaceutical compositions for use according to the present invention may be formulated in conventional manner using readily available pharmaceutical or veterinary aids. Thus the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsion, solutions, syrups, aerosols, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum, acacia, calcium phosphate, alginates, tragacanth, gelatin, calcium silicate, microcyrstalline cellulose, polyvinylpyrrolidine, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additional include lubricating agents, wetting agents, emulsifying agents, suspending agents, preserving agents, sweetening agents, flavouring agents, and the like. The formulations may be formulated so as to provide quick, sustained or delayed release of the active ingredient after administration to the patient by use of procedures well known in the art.

The compositions are preferably formulated in a unit dosage form, e.g. with each dosage containing from about 0.1 to about 500 mg of the active ingredient.

The precise dosage of the active ingredient and the length of the treatment will depend upon a number of actors including the age and weight of the patient, the specific condition being treated and its severity, and the route of administration. In general, an effective dose will be of the order of from about 0.01 mg/kg to about 20 mg/kg bodyweight per day, e.g. from about 0.05 to about 10 mg/kg per day, administered one or more times daily. Thus, an appropriate dose for an adult may be from 10 to 100 mg per day, e.g. 20 to 50 mg per day.

Administration may be any suitable method known in the art, including for example oral, parenteral (e.g.

intramuscular, subcutaneous, intraperitoneal or intravenous), rectal or topical administration.

Further exemplification of conditions which the invention may be applied and therapeutic agents which may be used is given below.

1.1. Wound Healing and Regulating Fibrosis

It is often desirable to increase the rate of healing in the case of acute wounds (such as penetrative injuries, burns, nerve damage or even wounds resulting from elective surgery), chronic wounds (such as diabetic, venous and decubitus ulceration) or for generally healing compromised individuals (for example the elderly). In these examples, the wounds can severely influence quality of life or even result in death and therefore the rate of healing often needs to be increased as much as is clinically possible. Where the rate of wound healing is increased, there is often an associated increase in scar formation but this may be of secondary importance compared to the desired increase in the rate of healing.

There are however other instances of wound healing in which fibrosis is regarded as a major problem in that the scar tissue which forms is not only unsightly but also causes problems in respect of growth, tissue functioning, movement etc. This is particularly true following injuries to children or following major burns. There are therefore situations where the regulation of scar formation is of primary importance and the rate of healing is only of secondary consideration. Examples of such situations are external wounds (especially of the skin) where excessive scarring may be detrimental to tissue function (for instance skin burns and wounds which impair flexibility of a joint). The reduction of scarring when cosmetic considerations are important (e.g. skin wounds of the face) is also highly desirable. In the skin, hypertrophic or keloid scars (particularly common in afro-Caribbean and mongoloid races) can cause functional and cosmetic impairment As well as external wounds (such as of the skin), internal scarring or fibrosis can be highly detrimental and specific examples include:

(i) Abdominal or peritoneal adhesions or strictures of the gut which may be life threatening scars or fibrotic conditions.

(ii) Scarring or fibrosis in the central nervous system (e.g. following a stroke or neurosurgery) which often leads to functional impairment and may inhibit neuronal reconnection.

(iii) Scarring or fibrosis in the eye (e.g. following injury or surgery of the cornea) may lead to visual impairment. For instance, scarring or fibrosis of the eye following glaucoma surgery can lead to a failure of the pressure equalising operation and may lead to a return of the disease conditions.

(iv) Fibrosis or scarring of ligaments or tendons can have serious effects on function.

Related to the above is the fact that there are a number of medical conditions in which excessive fibrosis leads to pathological derangement and malfunctioning of tissue. Examples include cirrhosis of the liver, glomerulonephritis, pulmonary fibrosis, scleroderma, systemic fibrosis, rheumatoid arthritis and proliferative vitreoretinopathy, in addition to wound healing. Systemic fibrosis may occur following wounding, ischaemia or some other pathological damage e.g. post-stroke scarring/fibrosis in the central nervous system, cardiac scarring/fibrosis following myocardial infarction. The present invention which may be used for the treatment of such conditions by regulating (i.e. preventing, inhibiting or reversing) fibrosis or scarring.

Whilst the above considerations mainly apply to conditions of man it will be appreciated that wound healing, scarring and fibrosis can also be problematic in other animals (especially domestic animals such as horses, dogs, cats etc). For instance abdominal wounds or adhesions are a major reason for having to put down horses, as are tendon and ligament damage leading to scarring or fibrosis.

In a first embodiment of the invention, the therapeutic agent may be a growth factor neutralising agent or agents specific against only fibrotic growth factors. The growth factor neutralising agent may be a growth factor neutralising antibody, for example antibodies to TGF-$\beta$1, TFG-$\beta$2, PDGF, IFN$\gamma$ or IL-1.

The growth factor neutralising agent may be a growth factor receptor blocking agent, for example a peptide containing the receptor binding site of the growth factors TGF-$\beta$1, TFG-$\beta$2, PDGF, IFN$\gamma$ or IL-1

The growth factor neutralising agent may also comprise a molecule which binds to the growth factor to inhibit receptor binding. For example when the growth factor is selected from TGF-$\beta$1, TFG-$\beta$2, PDGF, IFN$\gamma$ or IL-1, the molecule may be selected from Decorin, Biglycan, Fibromodulin, Lumican, Betaglycan, soluble type II TFG-$\beta$ Receptor and fragments or derivatives of these molecules which have binding affinity for the growth factors.

The growth factor neutralising agent may be an antisense oligonucleotide or ribozyme(s) to growth factor mRNA which both act to prevent mRNA from being translated.

The growth factor neutralising agent may also be a soluble form of the receptor or the growth factor binding domain of the receptor.

The growth factor neutralising agent may also be an aptmer which binds and neutralises the growth factor.

This embodiment of the invention is useful for inhibiting scar tissue formation during healing of wounds.

Examples of products which may be used in accordance with the first embodiment of the invention are disclosed in WO-A-92/17206, the disclosure of which is incorporated by reference.

In a second embodiment of the invention, the therapeutic agent is a non-fibrotic growth factor which may, for example, be TGF$\beta$-3, FGF-1, FGF-2, IL-4 or IL-10. Such products are useful particularly for preventing, inhibiting or reversing fibrosis. If desired, the gene product used in the second embodiment of the invention may be co-expressed with at least one anti-fibrotic agent, for example anti-TGF$\beta$-1/TGF$\beta$-2.

This embodiment of the invention is useful for inhibiting fibrosis during the healing of wounds and in other fibrotic conditions and disorders.

Further details as to gene products which may be used in accordance with the second embodiment of the invention are disclosed in WO-A-93/19769, the disclosure of which is incorporated by reference.

In accordance with a third embodiment of the invention the therapeutic agent is one which is capable of affecting the quantity of active growth factor or a protein associated therewith in a wound site at which the gene product is expressed. The agent may, for example, be specific to a non-fibrotic growth factor, e.g. selected from FGF-1, FGF-2, FGF-7, EGF, TGF$\alpha$, IL-4, IL-10, IL-12, IL-17 or TGF-$\beta_3$. Alternatively, the agent may be specific to a fibrotic growth factor, e.g. TGF-$\beta_1$, TGF-$\beta_2$, PDGFAA, PDGFBB, PDGFA, a member of the CTGF family, IL-1, IL-2, IL-6, IL-8 and TFN$\alpha$.

This embodiment of the invention may be used to promote the healing of wounds or fibrotic disorders with reduced scarring.

Further details relating to the third embodiment of the invention are given in WO-A-95 26203, the disclosure of which is incorporated herein by reference.

In a fourth embodiment of the invention, the therapeutic agent may be IL-4 or IL-10 or a fragment or a partially modified form thereof. By "fragment or partially modified form thereof" is meant a fragment or partial modified form of IL-4 or IL-10 which retains the anti-inflammatory healing functionality of IL-4 or IL-10.

IL-4 and IL-10 as well as fragments and partially modified forms thereof promote the healing of wounds or fibrotic disorders with reduced scarring as disclosed more fully in WO-A-97/05894 (PCT/GB96/01930), the disclosure of which is incorporated herein by reference.

In a fifth embodiment of the invention the therapeutic agent is a soluble betaglycan or a fragment or an analogue thereof which may be used for the healing of wounds or fibrotic disorders with reduced scarring. By "fragment or analogue" is meant a molecule which is capable of binding to TGF-$\beta_2$ performing the same role as soluble betaglycan. The "fragment or analogue" may, for example, comprise at least the TGF-$\beta$ binding fragment of soluble betaglycan.

This embodiment of the invention is useful for the treatment of wounds or fibrotic disorders with reduced scarring.

Reference is made to WO-A-97/05883 (PCT/GB 96/01840) for further disclosure relating to the use of soluble betaglycan or fragments or analogues thereof, the disclosure of GB 9516073.5 being incorporated herein by reference.

In sixth embodiment of the invention, the therapeutic agent is an inhibitor of Interferon-$\gamma$ (IFN-$\gamma$).

The inhibitor may, for example, be a neutralising antibody. Alternatively, the inhibitor may be anything which inhibits IFN-$\gamma$ from interacting with its receptor. It may, for example, be a molecule which mimics the IFN-$\gamma$ receptor binding sequence and which binds to the receptor but does not activate it, thereby competitively inhibiting the binding of IFN-$\gamma$ to the receptor and inhibiting the activation of the receptor.

This embodiment of the invention is useful for promoting the healing of wounds or fibrotic disorders with reduced scarring.

In an seventh embodiment of the invention, the therapeutic agent may be a stimulator of IFN-$\gamma$, i.e. an agent which increases the quantity or the efficacy of active IFN-$\gamma$ at a site. This may be IFN-$\gamma$ itself or an analogue of IFN-$\gamma$. Alternatively, it may be an inhibitor of IFN-$\gamma$ metabolism.

This embodiment of the invention is useful for promoting the healing of chronic wounds.

Further details relating to the sixth and seventh embodiments of the invention are disclosed in WO-A-97/07136, the disclosure of which is incorporated herein by reference.

In a eighth embodiment of the invention the therapeutic agent is an inhibitor of activation of at least one integrin receptor.

The inhibitor may bind to at least one receptor but not activate it.

The inhibitor may comprise an antibody. It may comprise an neutralising antibody. The antibody may bind specifically to at least one integrin receptor. It may bind specifically to the RGD peptide or an analogue thereof.

The inhibitor may comprise at least the RGD peptide or an analogue thereof.

The inhibitor may be any form of inhibitor which inhibits the activation of at least one integrin receptor. It may, for example, be a neutralising antibody specific to the RGD peptide of integrins, it may be a neutralising antibody specific to the integrin receptor, or it may contain the RGD peptide or an analogue thereof (e.g. a RGDS peptide or a mimitope of RGD) thereof which will bind to the integrin receptor and prevent the natural ligand from binding to it.

The receptor may be the GpIIb/IIIa platelet receptor. Therefore the inhibitor may be a GpIIb/IIIa platelet receptor inhibitor. The inhibitor may also comprise an RGD peptide or an analogue thereof.

The inhibitor may inhibit the binding of TGF-$\beta_1$ and/or platelets or leukocytes to fibrin and/or fibrinogen and/or fibronectin. It may for example be a fibrinogen receptor antagonist.

This embodiment of the invention is useful for the healing of wounds or fibrotic disorders with reduced scarring.

Further details relating to the eighth embodiment of the invention is given in WO-A-97/11718 (PCT/GB 96/02366), the disclosure of which is incorporated herein by reference.

In accordance with a ninth embodiment of the present invention, the therapeutic agent is an inhibitor of at least one convertase enzyme.

The inhibitor of the convertase enzyme may be a serine protease inhibitor.

This embodiment of the invention is useful for promoting the healing of wounds or fibrotic disorders with reduced scarring.

In accordance with a tenth embodiment of the present invention, the therapeutic agent may be a stimulator of Activin and/or Inhibin.

By "stimulator" is meant anything which may stimulate the quantity or efficacy of active activin and/or active inhibin at a site. This may be activin or inhibin itself or an analogue thereof. Such an analogue may, for example, have a longer half-life than activin or inhibin, or it may have a different binding affinity for its receptors. A fragment may comprise at least that part of activin or inhibin which is required to allow it to stimulate its receptors. Alternatively, it may, for example, be an inhibitor of activin metabolism or it may be a stimulator of activin synthesis. For example, it may be analogue of a fragment of activin or inhibin which is bound by a degraditive enzyme. It may be a mimotope made to a fragment of activin or inhibin which is bound by an enzyme which degrades it. Such a mimotope combined to the receptor site of the enzyme, competitively inhibiting the binding of activin or inhibin (as appropriate) to the enzyme and thereby inhibiting is degradation.

The stimulator may be an antagonist of an agonist of Activin and/or Inhibin. For example, the stimulator may be an antagonist of Follistatin.

This embodiment of the invention is useful for promoting the healing of wounds and fibrotic disorders with reduced scarring.

Further details regarding the tenth embodiment of the invention are given in WO-A-97/15321 (PCT/GB 96/02559), the disclosure of which is incorporated herein by reference.

In accordance with a eleventh embodiment of the present invention the therapeutic agent is one which modulates actin assembly and organisation. The product may for example be Gelsolin, Villin, CaPG, adseverin, flightless-1, advillin or derivatives thereof.

This embodiment of the invention is useful for increasing the rate of wound healing as well as improving scar quality.

Further details regarding the eleventh embodiment of the invention are disclosed in WO-A-98/24465, the disclosure of which is incorporated herein by reference.

In accordance with an twelfth embodiment of the present invention the therapeutic agent may be an agent which inhibits the activity of Interleukin-6.

Suitable inhibitors of IL-6 activity and thereby preferred proteins for use according to the twelfth embodiment of the invention include IL-6 Receptor antagonists (compounds which inhibit receptor activation by IL-6); compounds that disrupt signalling mediated by IL-6 (e.g. inhibitors of second messenger production, kinase inhibitors or modulators of gene expression); enzymes that specifically degrade IL-6 and inhibitors of IL-6 synthesis, neutralising antibodies to IL-6 (which would normally be high affinity antibodies used at a high concentration because low affinity/low concentrations of neutralising antibody are known to act as carriers and protective agents and so potentiate the activity of IL-6 (Heremans et al. Eur. J. Immunol. 22 p2395–2401, 1992), antisense oligonucleotides or ribozymes to IL-6, oligonucleotide aptmers which bind to and neutralise IL-6 or its receptor, molecules which bind to IL-6 and increase its clearance from a wound site.

The most preferred compounds for use as gene products for use according to the fifteenth embodiment of the invention are IL-6 Receptor antagonists and disrupters of IL-6 signalling.

This embodiment of the invention is useful for reducing fibrosis in wound healing and treatment of fibrotic disorders.

Further details relating to the twelfth embodiment of the invention are given in WO-A-98/36061 (PCT/GB98/00319), the disclosure of which is incorporated herein by reference.

In accordance with a thirteenth embodiment of the invention the therapeutic agent is Latency Associated Peptide or a functional analogue thereof.

This embodiment of the invention is useful for promoting wound healing.

Further details relating to the thirteenth embodiment of the invention are given in WO-A-98/35695 (PCT/GB98/00316), the disclosure of which is incorporated by reference.

In accordance with a fourteenth embodiment of the invention the therapeutic agent is Insulin Like Growth Factor I1 or a functional analogue thereof.

This embodiment of the invention is useful for promoting the rate of wound healing and for reducing or preventing scar formation and fibrosis.

In accordance with a fifteenth embodiment of the invention the therapeutic agent is a compound that influences the sex hormone system. The agent may be one which promotes oestrogen activity at the site of a wound for accelerating the healing of the wound. The agent promoting oestrogen activity may for example be oestrogen. Alternatively, the therapeutic agent may be one which modulates and androgenic activity, e.g. by promoting androgenic activity for accelerating the healing of wounds or by inhibiting androgenic activity for inhibiting fibrosis. Alternatively the therapeutic agent may be one which promotes progesterone activity for inhibiting fibrosis.

Further details relating to the fifteenth embodiment of the invention are given in WO-A-98/03180, the disclosure of which is incorporated herein by reference.

1.2 Ulcerative Colitis and Inflammatory Bowel Disease

The therapeutic agent which may be used in this embodiment of the invention include Sulphasalazine (and other 5-aminosalicylates), Metronidazole, Corticosteroids, Azathioprine, Cyclosporin A, and Methatrexate. Other agents would include ulcer healing drugs such as Omeprazole, Lansoprazole, and Rabeprazole.

1.3. Epilepsy

The therapeutic agent for use in the treatment of epilepsy may for example be Phenytoin, Phenobarbitone, Sodium Valporate, Topiramite.

1.4. Reperfusion Injury and Hypertension

Therapeutic agents which may be used in the treatment of these conditions include 1. Phosphodiasterase inhibitors
2. Modulators of immune response/apoptosis
3. Vasodilators, such as
  a) nitrates e.g. Isosorbide mono- or di-nitrate, or Glyceryl tri-nitrate, or.
  b) calcium antagonists, such as Verapamil/nifedipine, and Diltiazem
4. ACE inhibitors, such as Trandolapri, Captopril
5. Fibrinolytic agents, such as Streptokinase, Activase.
6. Anti platelets, such Aspirin, Ticolpidine.
7. Anti coagulants, such as Wolferin.
8. Beta blockers, such as Atenolol, Propranolol.
9. Xanthene Oxidase inhibitors, such as Elopurinol.
10. Free radical scavangers, such as Vitamin E, Manetol.

1.5. Cystic Fibrosis

Therapeutic agents which may be used in the treatment of these conditions include Ibuprofen and Prednisolone.

1.6. Psoriasis

Therapeutic agents which may be used in the treatment of these conditions include 1. Steroids such as Hydrocortisone, Prednisolone.
2. Vitamin D analogues
3. Psoralens
4. Antimitotics/immunosuppressants, such as Methotrexate, Retinoids, Cyclosporin A.

1.7. Rheumatoid Arthritis

Therapeutic agents which may be used in the treatment of these conditions include Sulfasalazine, Mesalazine. Penicillamine, Azathioprine, Chlorambucil, Myochrysine (sodium auro thiomalate), Hydroxychloroquine, Methotrexate, Cyclosporin Myocrisin and Neoral.

1.8. Diabetes

Therapeutic agents which may be used in the treatment of this condition include Acarbose, Aspirin, Indomethacin, Capropril and Prostaglandin Synthetase inhibitors.

1.9. Ischemia

Therapeutic agents that may be used in the treatment of this condition include peripheral vasodilators, such as Inositol Nicotinate, calcium antagonists, such as Niphedipine and Verapamil; anti platelets, such as Aspirin and Dipyridamole, ACE inhibitors, (Agniotensin Converting Enzyme) e.g. Ramapril and Trandolapril, fibrinolotic agents.

2. Therapeutic Agents 2.1. Non-steroidal anti-inflammatory agents

Examples of these agents which may be used include Ibuprofen, Naproxen, Fenoprofenb, Benoxaprofen, Sulindac, indomethacin, tolmetin and Diclofenac.

2.2. PDE Inhibitors

These may include, for example, PDE-4 inhibitors (Rolipram) or PDE-5 inhibitors, such as Zapronist, Dipyridamole or Sildenafil.

The conjugates in which the therapeutic agent is a PDE inhibitor (preferably a PDE-5 inhibitor) are used for the treatment of hypoxic conditions such as diabetes, rheumatoid arthritis, cancer and other hypoxic conditions as disclosed in the present specification.

2.3. Additional Agents

The therapeutic agent may be selected from immunosupressives, cell cycle specific drugs, cell cycle non-specific drugs, metalloprotease inhibitors and inhibitors of nitric oxide synthase.

These conjugates may be used as appropriate for any therapeutic application as disclosed in the present application, or as appropriate for any other therapeutic application.

In the case where the therapeutic agent is an immunosupressive, the bioreductive conjugate may be used in transplant surgery. The immunosupressive may, for example, be cyclosporin A.

Examples of cell cycle specific and cell cycle non-specific drugs include hormones and hormone analogues, anti-angiongenic, (e.g. endostatin, angiostatin), vascular targeted drugs (e.g. combreastatin), metalloprotease inhibitors.

The treatment of periodontitis may be effected using a bioreductive conjugate for which the therapeutic agent is a metalloprotease inhibitor.

The treatment of sepsis may be effected with an inhibitor of nitric oxide synthase.

What is claimed is:

1. A bioreductive conjugate comprising a bioreductive moiety with at least one therapeutic agent linked thereto and physiologically acceptable derivatives thereof wherein the bioreductive moiety incorporates an aromatic ring substituted with a nitro group and the conjugate is such that bioreduction of the nitro group causes release of the therapeutic agent by a through bond elimination and the residue of the bioreductive moiety to undergo an intramolecular cyclization reaction in which the nitrogen of the original nitro group provides an atom of the thus formed ring, wherein the therapeutic agent to be released on bioreduction is bonded to the aromatic ring via a side chain incorporating one or more double bonds which are located in the side chain between said therapeutic agent and the aromatic ring, which is/are conjugated to the aromatic ring, and which is/are displaceable to provide for elimination of said therapeutic moiety and formation of an arrangement of double bonds such that the residue of the bioreductive moiety is capable of undergoing the intramolecular cyclisation reaction, and wherein said conjugate is of the general formula (III)

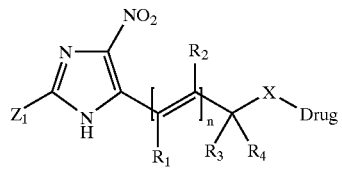

in which

Drug is a therapeutic agent;

X is a linker (which may be part of the drug) and is —NH,;

$R_1$, $R_2$, and $R_3$ are hydrogen, and $R_4$ is a substituted or unsubstituted alkyl n is 1 to 3; and $Z_1$ is hydrogen, substituted or unsubstituted alkyl, aryl, halide, amine, alkoxy, ether, ester, alcohol, phenol, nitro, amide, thiol, sulphate, phosphate, or phosphonate.

2. The conjugate as claimed in claim 1 wherein n=1.

3. The conjugate as claimed in claim 1 wherein the therapeutic agent is an anti-infective, analgesic, anaesthetic, anti-inflammatory or anti-neoplastic agent.

4. A therapeutic composition comprising the conjugate as claimed in claim 1 in conjunction with a therapeutically acceptable carrier.

5. The conjugate according to claim 1 wherein $R_4$ is a substituted or unsubstituted $C_{1-4}$alkyl.

6. The conjugate according to claim 1 wherein $Z_1$ is hydrogen, substituted or unsubstituted $C_{1-4}$alkyl, aryl, halide, amine, alkoxy, ether, ester, alcohol, phenol, nitro, amide, thiol, sulphate, phosphate, or phosphonate.

7. The conjugate according to claim 3 wherein the anti-infective agent is an antiobiotic or antiviral agent.

8. The conjugate as claimed in claim 1 wherein the bioreductive moeity is non-cytotoxic.

9. A method of therapeutic treatment, wherein the therapeutic treatment is for osteoarthritis, comprising administering to a subject in need thereof a therapeutically effective amount of the bioreductive conjugate as claimed in claim 1.

* * * * *